(12) United States Patent
Howell et al.

(10) Patent No.: US 12,741,119 B2
(45) Date of Patent: Sep. 22, 2026

(54) TWO-PIECE CATHETERS AND METHODS THEREOF

(71) Applicant: Bard Access Systems, Inc., Salt Lake City, UT (US)

(72) Inventors: Glade H. Howell, Draper, UT (US); Jason R. Stats, Layton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 775 days.

(21) Appl. No.: 17/360,746

(22) Filed: Jun. 28, 2021

(65) Prior Publication Data

US 2021/0402142 A1 Dec. 30, 2021

Related U.S. Application Data

(60) Provisional application No. 63/045,613, filed on Jun. 29, 2020.

(51) Int. Cl.
*A61M 25/00* (2006.01)
*A61M 25/01* (2006.01)
(Continued)

(52) U.S. Cl.
CPC .... *A61M 25/0097* (2013.01); *A61M 25/0606* (2013.01); *A61M 39/105* (2013.01); *A61M 39/12* (2013.01); *A61M 2025/0037* (2013.01)

(58) Field of Classification Search
CPC .......... A61M 25/0097; A61M 25/0606; A61M 39/12; A61M 2025/0037; A61M 25/0032;
(Continued)

(56) References Cited

U.S. PATENT DOCUMENTS 1,013,691 A 1/1912 Shields
3,225,762 A 12/1965 Guttman
(Continued)

FOREIGN PATENT DOCUMENTS

DE 102018102390 A1 8/2019
EP 0730880 A1 9/1996
(Continued)

OTHER PUBLICATIONS

PCT/US2020/056364 filed Oct. 19, 2020 International Preliminary Report on Patentability dated Apr. 19, 2022.
(Continued)

*Primary Examiner* — Chelsea E Stinson
*Assistant Examiner* — Hamza A Darb
(74) *Attorney, Agent, or Firm* — Rutan & Tucker LLP

(57) ABSTRACT

Disclosed herein are two-piece catheters and methods thereof. For example, a two-piece catheter can include a proximal catheter piece and a distal catheter piece. The proximal catheter piece includes a proximal catheter-hub piece and one or more extension legs respectively including one or more extension-leg lumens. Each extension leg of the one-or-more extension legs is coupled to the proximal catheter-hub piece by a distal-end portion of the extension leg. The distal catheter piece includes a distal catheter-hub piece and a catheter tube including one or more catheter-tube lumens. The catheter tube is coupled to the distal catheter-hub piece by a proximal-end portion of the catheter tube. The two-piece catheter has a connected state in which the proximal catheter-hub piece is connected to the distal catheter-hub piece such that the one-or-more catheter-tube lumens are respectively fluidly connected to the one-or-more extension-leg lumens across a two-piece catheter hub.

20 Claims, 7 Drawing Sheets

(51) Int. Cl.
*A61M 25/06* (2006.01)
*A61M 25/09* (2006.01)
*A61M 39/10* (2006.01)
*A61M 39/12* (2006.01)

(58) Field of Classification Search
CPC .......... A61M 25/0026; A61M 25/0043; A61M 25/0102; A61M 25/0113; A61M 25/065; A61M 25/09041; A61M 2025/0034; A61M 2210/12
See application file for complete search history.

(56) References Cited

U.S. PATENT DOCUMENTS 3,890,976 A 6/1975 Bazell et al.
4,205,675 A 6/1980 Vaillancourt
4,292,970 A 10/1981 Hession, Jr.
4,468,224 A 8/1984 Enzmann et al.
4,525,157 A 6/1985 Vaillancourt
4,581,019 A 4/1986 Curelaru et al.
5,017,259 A 5/1991 Kohsai
5,040,548 A 8/1991 Yock
5,057,073 A 10/1991 Martin
5,112,312 A 5/1992 Luther
5,120,317 A 6/1992 Luther
5,129,891 A 7/1992 Young
5,149,330 A * 9/1992 Brightbill ......... A61M 25/0026 604/533
5,167,623 A 12/1992 Cianci et al.
5,188,593 A 2/1993 Martin
5,195,962 A 3/1993 Martin et al.
5,207,650 A 5/1993 Martin
5,267,958 A 12/1993 Buchbinder et al.
5,295,970 A 3/1994 Clinton et al.
5,306,247 A 4/1994 Pfenninger
5,328,472 A 7/1994 Steinke et al.
5,350,358 A 9/1994 Martin
5,368,567 A 11/1994 Lee
5,370,615 A 12/1994 Johnson
5,378,230 A 1/1995 Mahurkar
5,380,290 A 1/1995 Makower et al.
5,389,087 A 2/1995 Miraki
5,405,341 A 4/1995 Martin
5,439,449 A 8/1995 Mapes et al.
5,443,457 A 8/1995 Ginn et al.
5,489,271 A 2/1996 Andersen
5,573,520 A 11/1996 Schwartz et al.
5,683,370 A 11/1997 Luther et al.
5,718,678 A 2/1998 Fleming, III
5,772,636 A 6/1998 Brimhall et al.
5,885,251 A 3/1999 Luther
5,919,164 A 7/1999 Andersen
5,947,940 A 9/1999 Beisel
5,957,893 A 9/1999 Luther et al.
6,066,489 A 5/2000 Fields et al.
6,074,379 A 6/2000 Prichard
6,206,849 B1 3/2001 Martin et al.
6,377,856 B1 4/2002 Carson
6,475,187 B1 11/2002 Gerberding
6,606,515 B1 8/2003 Windheuser et al.
6,716,228 B2 4/2004 Tal
6,726,659 B1 4/2004 Stocking et al.
6,819,951 B2 11/2004 Patel et al.
6,821,287 B1 11/2004 Jang
6,926,692 B2 8/2005 Katoh et al.
6,962,575 B2 11/2005 Tal
6,994,693 B2 2/2006 Tal
6,999,809 B2 2/2006 Currier et al.
7,025,746 B2 4/2006 Tal
7,029,467 B2 4/2006 Currier et al.
7,037,293 B2 5/2006 Carrillo et al.
7,074,231 B2 7/2006 Jang
7,141,050 B2 11/2006 Deal et al.
7,144,386 B2 12/2006 Korkor et al.
7,311,697 B2 12/2007 Osborne
7,364,566 B2 4/2008 Elkins et al.
7,377,910 B2 5/2008 Katoh et al.
7,390,323 B2 6/2008 Jang
D600,793 S 9/2009 Bierman et al.
D601,242 S 9/2009 Bierman et al.
D601,243 S 9/2009 Bierman et al.
7,594,911 B2 9/2009 Powers et al.
7,691,093 B2 4/2010 Brimhall
7,722,567 B2 5/2010 Tal
D617,893 S 6/2010 Bierman et al.
D624,643 S 9/2010 Bierman et al.
7,819,889 B2 10/2010 Healy et al.
7,857,788 B2 12/2010 Racz
D630,729 S 1/2011 Bierman et al.
7,909,797 B2 3/2011 Kennedy, II et al.
7,909,811 B2 3/2011 Agro et al.
7,922,696 B2 4/2011 Tal et al.
7,938,820 B2 5/2011 Webster et al.
7,967,834 B2 6/2011 Tal et al.
7,985,204 B2 7/2011 Katoh et al.
8,073,517 B1 12/2011 Burchman
8,105,286 B2 1/2012 Anderson et al.
8,192,402 B2 6/2012 Anderson et al.
8,202,251 B2 6/2012 Bierman et al.
8,206,356 B2 6/2012 Katoh et al.
8,372,107 B2 2/2013 Tupper
8,377,006 B2 2/2013 Tal et al.
8,454,577 B2 6/2013 Joergensen et al.
8,585,858 B2 11/2013 Kronfeld et al.
8,657,790 B2 2/2014 Tal et al.
8,672,888 B2 3/2014 Tal
8,696,645 B2 4/2014 Tal et al.
8,784,362 B2 7/2014 Boutilette et al.
8,827,958 B2 9/2014 Bierman et al.
8,876,704 B2 11/2014 Golden et al.
8,882,713 B1 11/2014 Call et al.
8,900,192 B2 12/2014 Anderson et al.
8,900,207 B2 12/2014 Uretsky
8,915,884 B2 12/2014 Tal et al.
8,956,327 B2 2/2015 Bierman et al.
9,023,093 B2 5/2015 Pal
9,138,252 B2 9/2015 Bierman et al.
9,180,275 B2 11/2015 Helm
9,265,920 B2 2/2016 Rundquist et al.
9,272,121 B2 3/2016 Piccagli
9,522,254 B2 12/2016 Belson
9,554,785 B2 1/2017 Walters et al.
9,566,087 B2 2/2017 Bierman et al.
9,675,784 B2 6/2017 Belson
9,713,695 B2 7/2017 Bunch et al.
9,764,117 B2 9/2017 Bierman et al.
9,770,573 B2 9/2017 Golden et al.
9,814,861 B2 11/2017 Boutillette et al.
9,820,845 B2 11/2017 von Lehe et al.
9,861,383 B2 1/2018 Clark
9,884,169 B2 2/2018 Bierman et al.
9,889,275 B2 2/2018 Voss et al.
9,913,585 B2 3/2018 McCaffrey et al.
9,913,962 B2 3/2018 Tal et al.
9,981,113 B2 5/2018 Bierman
10,010,312 B2 7/2018 Tegels
10,065,020 B2 9/2018 Gaur
10,098,724 B2 10/2018 Adams et al.
10,111,683 B2 10/2018 Tsamir et al.
10,118,020 B2 11/2018 Avneri et al.
10,130,269 B2 11/2018 McCaffrey et al.
10,220,184 B2 3/2019 Clark
10,220,191 B2 3/2019 Belson et al.
10,265,508 B2 4/2019 Baid
10,271,873 B2 4/2019 Steingisser et al.
10,376,675 B2 8/2019 Mitchell et al.
10,675,440 B2 6/2020 Abitabilo et al.
10,806,901 B2 10/2020 Burkholz et al.
2002/0040231 A1 4/2002 Wysoki
2002/0198492 A1 12/2002 Miller et al.
2003/0036712 A1 2/2003 Heh et al.
2003/0060863 A1 3/2003 Dobak
2003/0088212 A1 5/2003 Tal
2003/0100849 A1 5/2003 Jang

(56) References Cited

U.S. PATENT DOCUMENTS

2003/0153874 A1 8/2003 Tal
2003/0158514 A1 8/2003 Tal
2004/0116901 A1 6/2004 Appling
2004/0122418 A1 6/2004 Voorhees
2004/0193093 A1 9/2004 Desmond
2004/0199122 A1 10/2004 Bierman et al.
2004/0230178 A1 11/2004 Wu
2005/0004554 A1 1/2005 Osborne
2005/0245882 A1 11/2005 Elkins et al.
2005/0261665 A1* 11/2005 Voorhees .......... A61M 25/0097 604/535
2005/0283221 A1 12/2005 Mann et al.
2006/0009740 A1 1/2006 Higgins et al.
2006/0015086 A1 1/2006 Rasmussen et al.
2006/0074380 A1 4/2006 Mogensen et al.
2006/0116629 A1 6/2006 Tal et al.
2006/0129100 A1 6/2006 Tal
2006/0129130 A1 6/2006 Tal et al.
2007/0078412 A1 4/2007 McGuckin et al.
2008/0045894 A1 2/2008 Perchik et al.
2008/0125744 A1 5/2008 Treacy
2008/0125748 A1 5/2008 Patel
2008/0255447 A1 10/2008 Bourang et al.
2008/0262430 A1 10/2008 Anderson et al.
2008/0262431 A1 10/2008 Anderson et al.
2008/0294111 A1 11/2008 Tal et al.
2008/0306465 A1 12/2008 Bailey et al.
2008/0312578 A1 12/2008 DeFonzo et al.
2009/0221961 A1 9/2009 Tal et al.
2009/0270889 A1 10/2009 Tal et al.
2010/0125249 A1 5/2010 Rosenberg et al.
2010/0256487 A1 10/2010 Hawkins et al.
2010/0305474 A1 12/2010 DeMars et al.
2011/0004162 A1 1/2011 Tal
2011/0009827 A1 1/2011 Bierman et al.
2011/0021994 A1 1/2011 Anderson et al.
2011/0066142 A1 3/2011 Tal et al.
2011/0144620 A1 6/2011 Tal
2011/0152836 A1 6/2011 Riopelle et al.
2011/0202006 A1 8/2011 Bierman et al.
2011/0251559 A1 10/2011 Tal et al.
2011/0270192 A1 11/2011 Anderson et al.
2011/0319825 A1 12/2011 Goral et al.
2012/0041371 A1 2/2012 Tal et al.
2012/0065590 A1 3/2012 Bierman et al.
2012/0078231 A1 3/2012 Hoshinouchi
2012/0130411 A1 5/2012 Tal et al.
2012/0130415 A1 5/2012 Tal et al.
2012/0157854 A1 6/2012 Kurrus et al.
2012/0220942 A1 8/2012 Hall et al.
2012/0232498 A1 9/2012 Ma et al.
2012/0239005 A1 9/2012 Conway et al.
2012/0283640 A1 11/2012 Anderson et al.
2012/0316500 A1 12/2012 Bierman et al.
2013/0053826 A1 2/2013 Shevgoor
2013/0123704 A1 5/2013 Bierman et al.
2013/0158338 A1 6/2013 Kelly et al.
2013/0188291 A1 7/2013 Vardiman
2013/0237931 A1 9/2013 Tal et al.
2013/0306079 A1 11/2013 Tracy
2014/0025036 A1 1/2014 Bierman et al.
2014/0081210 A1 3/2014 Bierman et al.
2014/0100552 A1 4/2014 Gallacher et al.
2014/0207052 A1 7/2014 Tal et al.
2014/0207069 A1 7/2014 Bierman et al.
2014/0214005 A1 7/2014 Belson
2014/0257111 A1 9/2014 Yamashita et al.
2014/0276432 A1 9/2014 Bierman et al.
2014/0276599 A1 9/2014 Cully et al.
2015/0051536 A1 2/2015 Mendels et al.
2015/0080939 A1 3/2015 Adams et al.
2015/0112310 A1 4/2015 Call et al.
2015/0126930 A1 5/2015 Bierman et al.
2015/0148595 A1 5/2015 Bagwell et al.
2015/0190168 A1 7/2015 Bierman et al.
2015/0196210 A1 7/2015 McCaffrey et al.
2015/0224287 A1 8/2015 Bian et al.
2015/0283357 A1 10/2015 Lampropoulos et al.
2015/0297868 A1 10/2015 Tal et al.
2015/0320969 A1 11/2015 Haslinger et al.
2015/0351793 A1 12/2015 Bierman et al.
2015/0359549 A1 12/2015 Lenker et al.
2015/0359998 A1 12/2015 Carmel et al.
2016/0067449 A1 3/2016 Misener et al.
2016/0082223 A1 3/2016 Barnell
2016/0114124 A1 4/2016 Tal
2016/0220786 A1 8/2016 Mitchell et al.
2016/0306393 A1 10/2016 Huitema
2016/0325073 A1 11/2016 Davies et al.
2016/0338728 A1 11/2016 Tal
2016/0346503 A1 12/2016 Jackson et al.
2017/0035990 A1 2/2017 Swift
2017/0043126 A1* 2/2017 Jones .................. A61M 39/045
2017/0072165 A1 3/2017 Lim et al.
2017/0120000 A1* 5/2017 Osypka .............. A61M 39/105
2017/0128700 A1 5/2017 Roche Rebollo
2017/0143890 A1 5/2017 Nardeo
2017/0172653 A1 6/2017 Urbanski et al.
2017/0239443 A1 8/2017 Abitabilo et al.
2017/0273628 A1 9/2017 Ofek et al.
2017/0273713 A1 9/2017 Shah et al.
2017/0296792 A1 10/2017 Ornelas Vargas et al.
2017/0326339 A1 11/2017 Bailey et al.
2017/0326349 A1 11/2017 Pagano, II et al.
2017/0361070 A1 12/2017 Hivert
2018/0021545 A1 1/2018 Mitchell et al.
2018/0116690 A1 5/2018 Sarabia et al.
2018/0117284 A1 5/2018 Appling et al.
2018/0133438 A1 5/2018 Hulvershorn et al.
2018/0154062 A1 6/2018 DeFonzo et al.
2018/0154112 A1 6/2018 Chan et al.
2018/0214674 A1 8/2018 Ebnet et al.
2018/0296799 A1 10/2018 Horst et al.
2018/0296804 A1 10/2018 Bierman
2019/0015646 A1 1/2019 Matlock et al.
2019/0060616 A1 2/2019 Solomon
2019/0076167 A1 3/2019 Fantuzzi et al.
2019/0134349 A1 5/2019 Cohn et al.
2019/0201665 A1 7/2019 Turpin
2019/0255294 A1 8/2019 Mitchell et al.
2019/0276268 A1 9/2019 Akingba
2019/0321590 A1 10/2019 Burkholz et al.
2020/0016374 A1 1/2020 Burkholz et al.
2020/0121211 A1 4/2020 Tutino
2021/0069471 A1 3/2021 Howell
2021/0121661 A1 4/2021 Howell
2021/0121667 A1 4/2021 Howell
2021/0128879 A1 5/2021 Seidenberger
2021/0322729 A1 10/2021 Howell
2021/0330941 A1 10/2021 Howell et al.
2021/0330942 A1 10/2021 Howell
2021/0361915 A1 11/2021 Howell et al.
2021/0402149 A1 12/2021 Howell
2021/0402153 A1 12/2021 Howell et al.
2022/0001138 A1 1/2022 Howell
2022/0032013 A1 2/2022 Howell et al.
2023/0256199 A1 8/2023 Howell
2023/0256209 A1 8/2023 Mckinnon et al.

FOREIGN PATENT DOCUMENTS

EP 2061385 A1 5/2009
EP 1458437 B1 3/2010
EP 2248549 A2 11/2010
EP 2319576 A1 5/2011
EP 2366422 A1 9/2011
EP 2486880 A2 8/2012
EP 2486881 A2 8/2012
EP 2486951 A2 8/2012
EP 2512576 A2 10/2012
EP 2152348 B1 2/2015
EP 2896424 A1 7/2015
EP 3093038 B1 5/2019
EP 2260897 B1 9/2019

(56) References Cited

FOREIGN PATENT DOCUMENTS

| | | | |
|---|---|---|---|
| GB | 1273547 | A | 5/1972 |
| WO | 94/21315 | A1 | 9/1994 |
| WO | 95/32009 | A2 | 11/1995 |
| WO | 98/44979 | A1 | 10/1998 |
| WO | 98/53871 | A1 | 12/1998 |
| WO | 99/12600 | A1 | 3/1999 |
| WO | 99/26681 | A1 | 6/1999 |
| WO | 2003008020 | A1 | 1/2003 |
| WO | 2003057272 | A2 | 7/2003 |
| WO | 2003066125 | A2 | 8/2003 |
| WO | 2004050144 | A2 | 6/2004 |
| WO | 2006055288 | A2 | 5/2006 |
| WO | 2006055780 | A2 | 5/2006 |
| WO | 2007046850 | A2 | 4/2007 |
| WO | 2008033983 | A1 | 3/2008 |
| WO | 2008092029 | A2 | 7/2008 |
| WO | 2008/131300 | A2 | 10/2008 |
| WO | 2008131289 | A2 | 10/2008 |
| WO | 2009114833 | A1 | 9/2009 |
| WO | 2009114837 | A2 | 9/2009 |
| WO | 2010/048449 | A2 | 4/2010 |
| WO | 2010056906 | A2 | 5/2010 |
| WO | 2010083467 | A2 | 7/2010 |
| WO | 2010/132608 | A2 | 11/2010 |
| WO | 2011081859 | A2 | 7/2011 |
| WO | 2011097639 | A2 | 8/2011 |
| WO | 2011146764 | A1 | 11/2011 |
| WO | 2012068162 | A2 | 5/2012 |
| WO | 2012068166 | A2 | 5/2012 |
| WO | 2012135761 | A1 | 10/2012 |
| WO | 2012162677 | A1 | 11/2012 |
| WO | 2013026045 | A1 | 2/2013 |
| WO | 2013138519 | A1 | 9/2013 |
| WO | 2014006403 | A1 | 1/2014 |
| WO | 2014/100392 | A1 | 6/2014 |
| WO | 2014113257 | A2 | 7/2014 |
| WO | 2014152005 | A2 | 9/2014 |
| WO | 2014197614 | A2 | 12/2014 |
| WO | 2015057766 | A1 | 4/2015 |
| WO | 2015/166157 | A1 | 11/2015 |
| WO | 2016110824 | A1 | 7/2016 |
| WO | 2016123278 | A1 | 8/2016 |
| WO | 2016139590 | A1 | 9/2016 |
| WO | 2016139597 | A2 | 9/2016 |
| WO | 2016176065 | A1 | 11/2016 |
| WO | 2017127074 | A1 | 7/2017 |
| WO | 2018089275 | A1 | 5/2018 |
| WO | 2018089285 | A1 | 5/2018 |
| WO | 2018089385 | A1 | 5/2018 |
| WO | 2018191547 | A1 | 10/2018 |
| WO | 2018213148 | A1 | 11/2018 |
| WO | 2018218236 | A1 | 11/2018 |
| WO | 2019/034320 | A1 | 2/2019 |
| WO | 2019/040801 | A1 | 2/2019 |
| WO | 2019/146026 | A1 | 8/2019 |
| WO | 2019199734 | A1 | 10/2019 |
| WO | 2020069395 | A1 | 4/2020 |
| WO | 2021050302 | A1 | 3/2021 |
| WO | 2021/077103 | A1 | 4/2021 |
| WO | 2021062023 | A1 | 4/2021 |
| WO | 2021081205 | A1 | 4/2021 |
| WO | 2021086793 | A1 | 5/2021 |
| WO | 2022133297 | A1 | 6/2022 |
| WO | 2023158613 | A1 | 8/2023 |
| WO | 2023158709 | A1 | 8/2023 |

OTHER PUBLICATIONS

PCT/US2020/056364 filed Oct. 19, 2020 International Search Report and Written Opinion dated Jan. 19, 2021.

PCT/US2020/056864 filed Oct. 22, 2020 International Preliminary Report on Patentability dated Apr. 26, 2022.

PCT/US2020/056864 filed Oct. 22, 2020 International Search Report and Written Opinion dated Jan. 14, 2021.

PCT/US2020/057397 filed Oct. 26, 2020 International Search Report and Written Opinion dated Mar. 10, 2021.

PCT/US2021/036445 filed Jun. 8, 2021 International Search Report and Written Opinion dated Dec. 21, 2021.

U.S. Appl. No. 17/077,728, filed Oct. 22, 2020 Non-Final Office Action dated Feb. 9, 2022.

PCT/US2021/039398 filed Jun. 28, 2021 International Search Report and Written Opinion dated Nov. 5, 2021.

U.S. Appl. No. 17/074,405, filed Oct. 19, 2020 Non-Final Office Action dated Mar. 31, 2023.

U.S. Appl. No. 17/074,405, filed Oct. 19, 2020 Restriction Requirement dated Jan. 17, 2023.

U.S. Appl. No. 17/077,728, filed Oct. 22, 2020 Final Office Action dated Jun. 14, 2022.

U.S. Appl. No. 17/077,728, filed Oct. 22, 2020 Non-Final Office Action dated Feb. 15, 2023.

U.S. Appl. No. 17/080,578, filed Oct. 26, 2020 Non-Final Office Action dated Mar. 31, 2023.

U.S. Appl. No. 17/080,578, filed Oct. 26, 2020 Restriction Requirement dated Dec. 15, 2022.

U.S. Appl. No. 17/342,285, filed Jun. 8, 2021 Restriction Requirement dated May 2, 2023.

PCT/US2023/012931 filed Feb. 13, 2023 International Search Report and Written Opinion dated May 25, 2023.

PCT/US2023/013165 filed Feb. 15, 2023 International Search Report and Written Opinion dated Jun. 13, 2023.

U.S. Appl. No. 17/077,728, filed Oct. 22, 2020 Final Office Action dated Aug. 28, 2023.

U.S. Appl. No. 17/342,285, filed Jun. 8, 2021 Non-Final Office Action dated Aug. 1, 2023.

EP 20882316.1 filed Apr. 21, 2022 Extended European Search Report dated Oct. 16, 2023.

EP 20878324.1 filed Mar. 11, 2022 Extended European Search Report dated Jan. 3, 2024.

U.S. Appl. No. 17/074,405, filed Oct. 19, 2020 Final Office Action dated Jan. 18, 2024.

U.S. Appl. No. 17/077,728, filed Oct. 22, 2020 Examiner's Answer dated Mar. 7, 2024.

U.S. Appl. No. 17/080,578, filed Oct. 26, 2020 Advisory Action dated Apr. 11, 2024.

U.S. Appl. No. 17/080,578, filed Oct. 26, 2020 Final Office Action dated Feb. 27, 2024.

U.S. Appl. No. 17/342,285, filed Jun. 8, 2021 Final Office Action dated Apr. 25, 2024.

U.S. Appl. No. 17/342,285, filed Jun. 8, 2021 Non-Final Office Action dated Dec. 22, 2023.

U.S. Appl. No. 17/342,285, filed Jun. 8, 2021 Non-Final Office Action dated Sep. 28, 2024.

U.S. Appl. No. 17/077,728, filed Oct. 22, 2020 Board Decision dated Aug. 20, 2025.

U.S. Appl. No. 17/080,578, filed Oct. 26, 2020 Non-Final Office Action dated Oct. 17, 2025.

U.S. Appl. No. 17/342,285, filed Jun. 8, 2021 Non-Final Office Action dated Aug. 27, 2025.

* cited by examiner

PROXIMAL
144
E
E
160
156
D
D
C
C
146
B
B
114
A
A
142
DISTAL
148
152

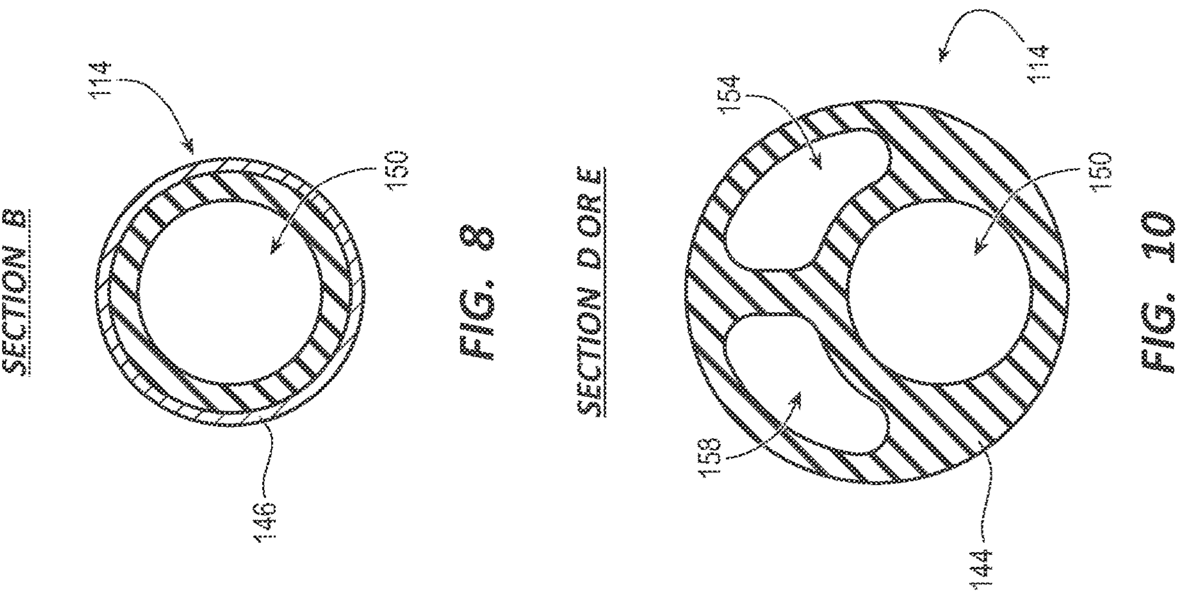
FIG. 8
FIG. 10
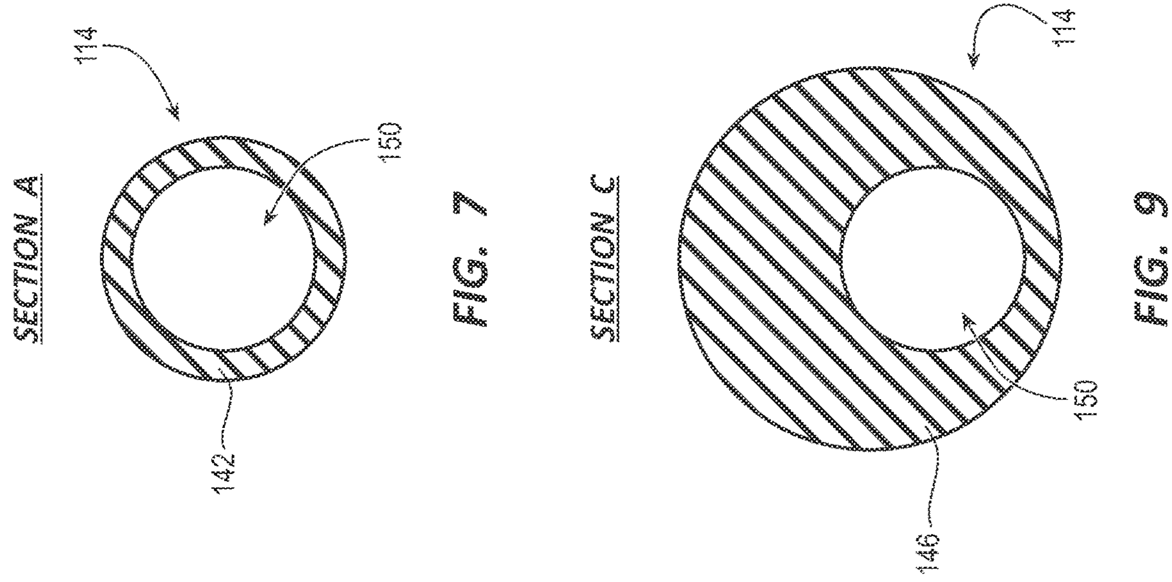
FIG. 7
FIG. 9

TWO-PIECE CATHETERS AND METHODS THEREOF

PRIORITY

This application claims the benefit of priority to U.S. Provisional Application No. 63/045,613, filed Jun. 29, 2020, which is incorporated by reference in its entirety into this application.

BACKGROUND

Existing catheters are manufactured as whole ready-to-use catheters. Such catheters can have lengths ranging from 30 to 40 cm as measured from the proximal end to the distal end of any such catheter. Rapidly insertable central catheters ("RICCs") currently under development are introduced over introducer needles; however, introduction of the RICCs over 30-40 cm introducer needles could be cumbersome for some clinicians. In addition, it could be difficult to timely discern whether blood flashback has occurred and access to a blood-vessel lumen established during any given RICC introduction with a 30-40 cm introducer needle. As such, catheters such as RICCs would benefit from being shorter than the existing catheters for at least their introduction.

Disclosed herein are two-piece catheters and methods thereof that address the foregoing need.

SUMMARY

Disclosed herein is a two-piece catheter including, in some embodiments, a proximal catheter piece and a distal catheter piece. The proximal catheter piece includes a proximal catheter-hub piece of a two-piece catheter hub and one or more extension legs. The one-or-more extension legs respectively include one or more extension-leg lumens. Each extension leg of the one-or-more extension legs is coupled to the proximal catheter-hub piece by a distal-end portion of the extension leg. The distal catheter piece includes a distal catheter-hub piece of the two-piece catheter hub and a catheter tube. The catheter tube includes one or more catheter-tube lumens. The catheter tube is coupled to the distal catheter-hub piece by a proximal-end portion of the catheter tube. The two-piece catheter has a connected state in which the proximal catheter-hub piece is connected to the distal catheter-hub piece such that the one-or-more catheter-tube lumens are respectively fluidly connected to the one-or-more extension-leg lumens across the two-piece catheter hub.

In some embodiments, the proximal catheter-hub piece includes one or more rigid tubes respectively disposed in one or more proximal catheter-hub lumens. The one-or-more rigid tubes extend from a distal end of the proximal catheter-hub piece.

In some embodiments, the distal catheter-hub piece includes one or more seals respectively disposed in one or more distal catheter-hub lumens. The one-or-more seals are configured to sit between the one-or-more rigid tubes and the one-or-more distal catheter-hub lumens, respectively, in the connected state of the two-piece catheter assembly.

In some embodiments, the distal catheter-hub piece includes one or more rigid tubes respectively disposed in one or more distal catheter-hub lumens. The one-or-more rigid tubes extend from a proximal end of the distal catheter-hub piece.

In some embodiments, the proximal catheter-hub piece includes one or more seals respectively disposed in one or more proximal catheter-hub lumens. The one-or-more seals are configured to sit between the one-or-more rigid tubes and the one-or-more proximal catheter-hub lumens, respectively, in the connected state of the two-piece catheter assembly.

In some embodiments, the distal catheter-hub piece includes an integral clip having tabbed arms proximally extending from the distal catheter-hub piece. The proximal catheter-hub piece includes surface recesses configured to seat tabs of the arms therein in the connected state of the two-piece catheter assembly.

In some embodiments, the proximal catheter-hub piece includes surface-undercut grooves configured to seat tips of the arms therein in the connected state of the two-piece catheter assembly.

In some embodiments, the arms extend from major sides of the distal catheter-hub piece and the surface recesses are in major surfaces of the proximal catheter-hub piece.

In some embodiments, the arms extend from minor sides of the distal catheter-hub piece and the surface recesses are in minor surfaces of the proximal catheter-hub piece.

In some embodiments, the proximal catheter-hub piece includes an integral clip having tabbed arms distally extending from the proximal catheter-hub piece. The distal catheter-hub piece includes surface recesses configured to seat tabs of the arms therein in the connected state of the two-piece catheter assembly.

In some embodiments, the distal catheter-hub piece includes surface-undercut grooves configured to seat tips of the arms therein in the connected state of the two-piece catheter assembly.

In some embodiments, the arms extend from major sides of the proximal catheter-hub piece and the surface recesses are in major surfaces of the distal catheter-hub piece.

In some embodiments, the arms extend from minor sides of the proximal catheter-hub piece and the surface recesses are in minor surfaces of the distal catheter-hub piece.

In some embodiments, the two-piece catheter includes a set of three lumens in the connected state of the two-piece catheter assembly. The set of three lumens includes a primary lumen, a secondary lumen, and a tertiary lumen.

In some embodiments, the primary lumen has a primary-lumen aperture in a distal end of the two-piece catheter, the secondary lumen has a secondary-lumen aperture in a side of the catheter tube proximal of the primary-lumen aperture, and the tertiary lumen has a tertiary-lumen aperture in the side of the catheter tube proximal of the secondary-lumen aperture.

Also disclosed is a method of using the two-piece catheter including, in some embodiments, a catheter-obtaining step, a needle tract-establishing step, a needle-withdrawing step, and a catheter hub-clipping step. The catheter-obtaining step includes obtaining a two-piece catheter including a distal catheter piece and a proximal catheter piece. The distal catheter piece includes a catheter tube coupled to a distal catheter-hub piece by a proximal-end portion of the catheter tube. The needle tract-establishing step includes establishing a needle tract from an area of skin to a blood-vessel lumen of a patient with an introducer needle disposed in an introducing lumen of the distal catheter piece. The introducer needle is disposed in the distal catheter piece such that a needle tip of the introducer needle extends out of an introducing-lumen aperture of the introducing lumen. The needle-withdrawing step includes withdrawing the introducer needle from the introducing lumen. The catheter hub-clipping step includes clipping together the distal catheter-hub piece and a proximal catheter-hub piece. Upon clipping together the distal catheter-hub piece and the proximal catheter-hub piece, one or more catheter-tube lumens of the catheter tube respectively connect to one or more extension-leg lumens of one or more extension legs coupled to the proximal catheter-hub piece of the proximal catheter piece.

In some embodiments, the catheter hub-clipping step includes clipping an integral clip of the distal catheter-hub piece onto the proximal catheter-hub piece. Upon clipping the integral clip of the distal catheter-hub piece onto the proximal catheter-hub piece, tabs of arms of the integral clip seat in surface recesses in major or minor surfaces of the proximal catheter-hub piece.

In some embodiments, the catheter hub-clipping step includes clipping an integral clip of the proximal catheter-hub piece onto the distal catheter-hub piece. Upon clipping the integral clip of the proximal catheter-hub piece onto the distal catheter-hub piece, tabs of arms of the integral clip seat in surface recesses in major or minor surfaces of the distal catheter-hub piece.

In some embodiments, the method further includes an access guidewire-advancing step, a first catheter-advancing step, and an access guidewire-withdrawing step. The access guidewire-advancing step includes advancing an access guidewire disposed in a needle lumen of the introducer needle into the blood-vessel lumen beyond the needle tip. The first catheter-advancing step includes advancing a distal-end portion of a first section of the catheter tube into the blood-vessel lumen over the introducer needle using the access guidewire as a guide. The access guidewire-withdrawing step includes withdrawing the access guidewire together with the introducer needle when withdrawing the introducer needle from the introducing lumen.

In some embodiments, the method further includes a maneuver guidewire-advancing step, a second catheter-advancing step, and a maneuver guidewire-withdrawing step. The maneuver guidewire-advancing step includes advancing a maneuver guidewire into the blood-vessel lumen and to a target location by way of a primary lumen of the two-piece catheter. The primary lumen is established by clipping together the distal catheter-hub piece and the proximal catheter-hub piece. The second catheter-advancing step includes advancing a remainder of the distal-end portion of the first section of the catheter tube into the blood-vessel lumen up to a proximal-end portion of a second section of the catheter tube using the maneuver guidewire as a guide. Advancing the catheter in accordance with the second catheter-advancing step is stopped when a distal end of the two-piece catheter arrives at the target location. The maneuver guidewire-withdrawing step includes withdrawing the maneuver guidewire and leaving the two-piece catheter in place in the patient.

These and other features of the concepts provided herein will become more apparent to those of skill in the art in view of the accompanying drawings and following description, which describe particular embodiments of such concepts in greater detail.

DRAWINGS

FIG. 7 illustrates a first transverse cross section of the catheter tube of FIG. 6 in accordance with some embodiments.

FIG. 8 illustrates a second transverse cross section of the catheter tube of FIG. 6 in accordance with some embodiments.

FIG. 9 illustrates a third transverse cross section of the catheter tube of FIG. 6 in accordance with some embodiments.

FIG. 10 illustrates a fourth transverse cross section of the catheter tube of FIG. 6 in accordance with some embodiments.

DESCRIPTION

Figure 1:
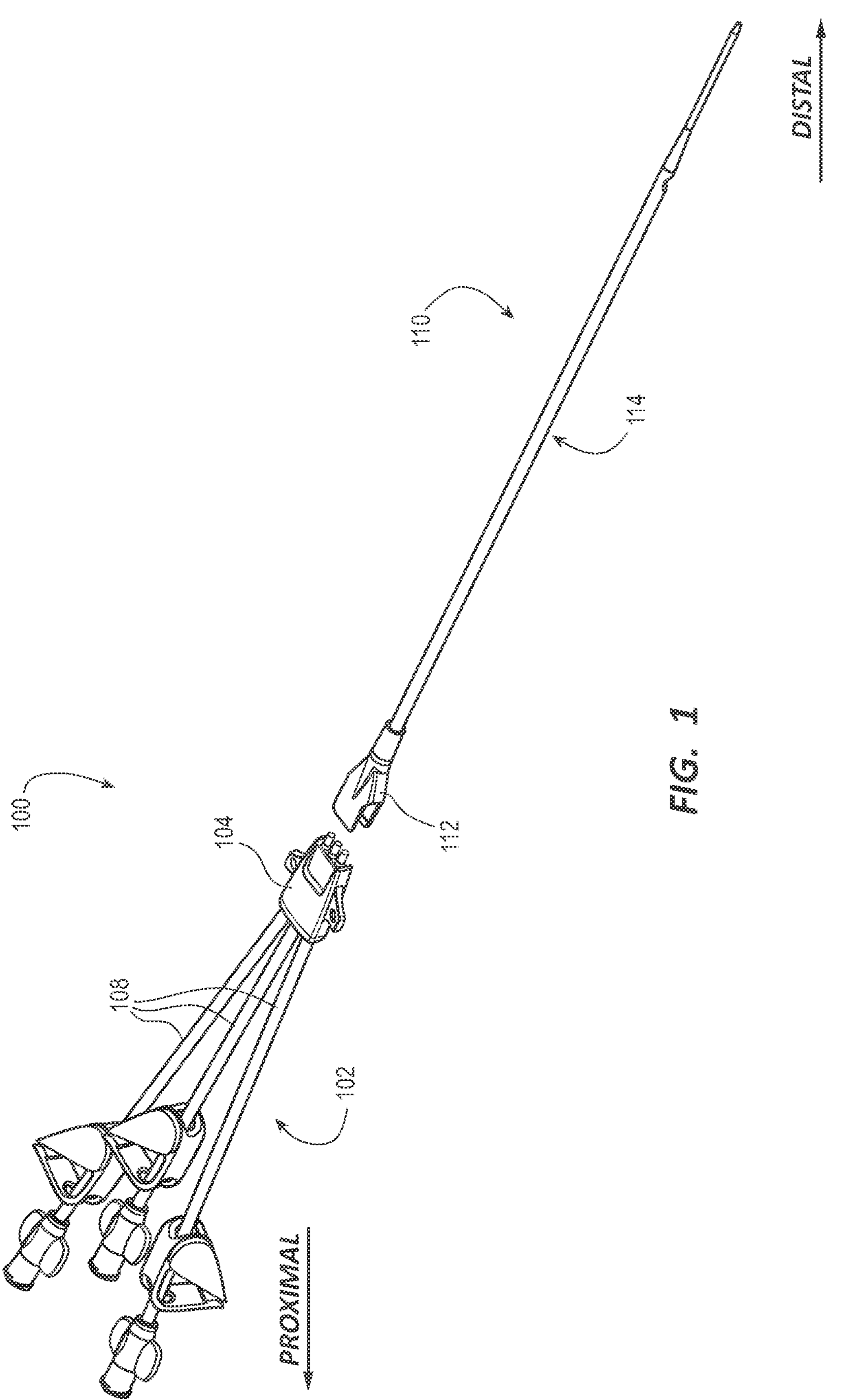
FIG. 1 illustrates a two-piece catheter in an unconnected state in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

As set forth above, existing catheters are manufactured as whole ready-to-use catheters having lengths ranging from 30 to 40 cm. The RICCs currently under development are introduced over introducer needles; however, introduction of the RICCs over 30-40 cm introducer needles could be cumbersome for some clinicians. In addition, it could be difficult to timely discern whether blood flashback has occurred and access to a blood-vessel lumen established during any given RICC introduction with a 30-40 cm introducer needle. As such, catheters such as RICCs, but not limited thereto, would benefit from being shorter than the existing catheters for at least their introduction. Disclosed herein are two-piece catheters and methods thereof that address the foregoing need.

Unless defined otherwise, all technical and scientific terms used herein have the same meaning as commonly understood by those of ordinary skill in the art.

Two-Piece Catheters

Figure 2:
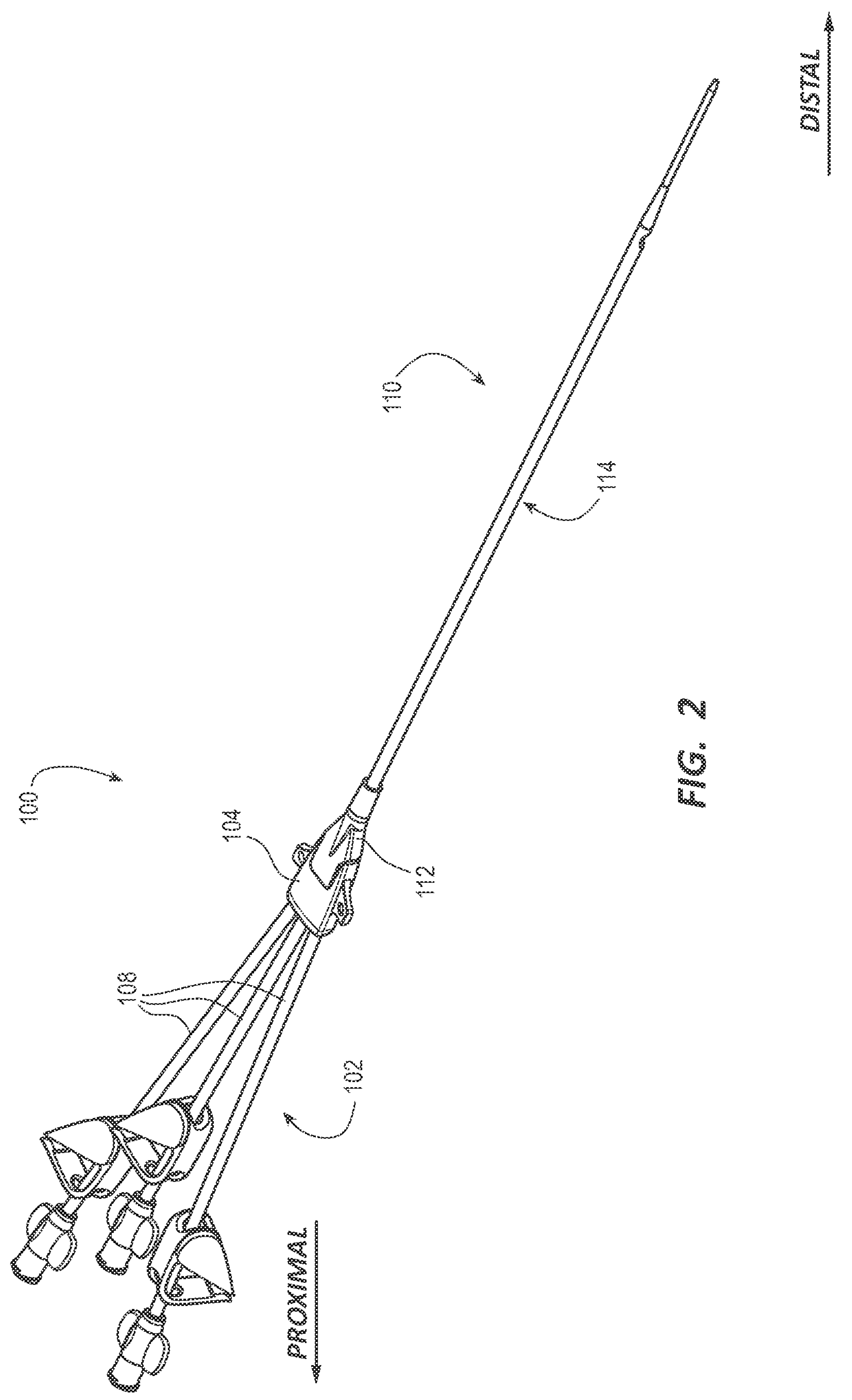
FIG. 2 illustrates the two-piece catheter in a connected state in accordance with some embodiments.

FIGS. 1 and 2 illustrate a two-piece catheter 100 in an unconnected state and a connected state in accordance with some embodiments.

As shown, the two-piece catheter 100 includes, in such embodiments, two pieces including a proximal catheter piece 102 and a distal catheter piece 110. It should be understood the two-piece catheter 100 can include different pieces or additional pieces to those in the illustrated embodiments. Indeed, the "two pieces" of the two-piece catheter 100 generally refer to at least two pieces resulting from dividing such a catheter along its length, in this case, at the two-piece catheter hub 106 set forth below.

The proximal catheter piece 102 includes a proximal catheter-hub piece 104 of a two-piece catheter hub 106 and one or more extension legs 108. The distal catheter piece 110 includes a distal catheter-hub piece 112 of the two-piece catheter hub 106 and a catheter tube 114. The two-piece catheter hub 106 is described first followed by description for the catheter tube 114, the one-or-more extension legs 108, and other aspects of the two-piece catheter 100.

Figure 3:
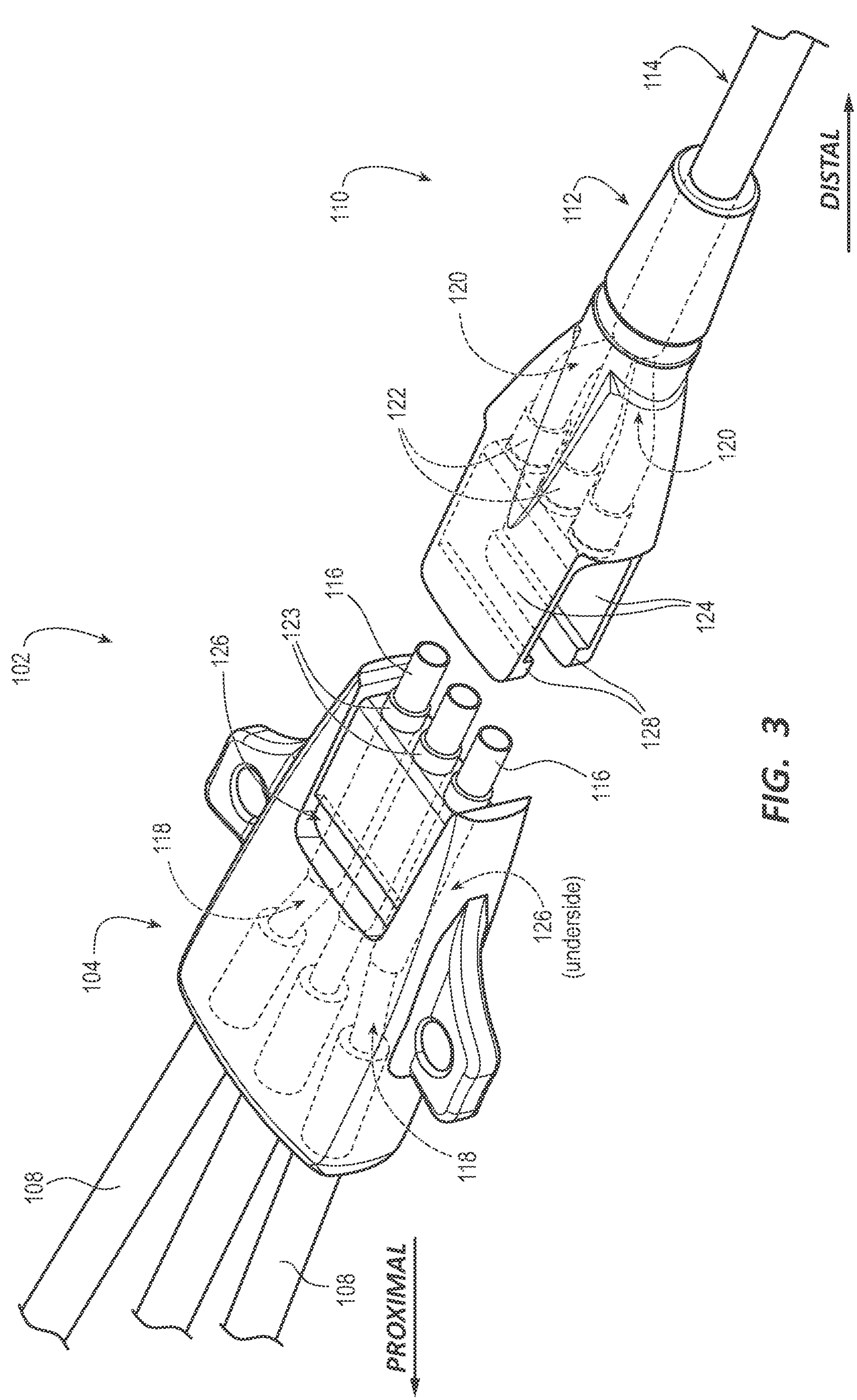
FIG. 3 illustrates a proximal catheter-hub piece and a distal catheter-hub piece of a two-piece catheter hub in the unconnected state in accordance with some embodiments.
Figure 4:
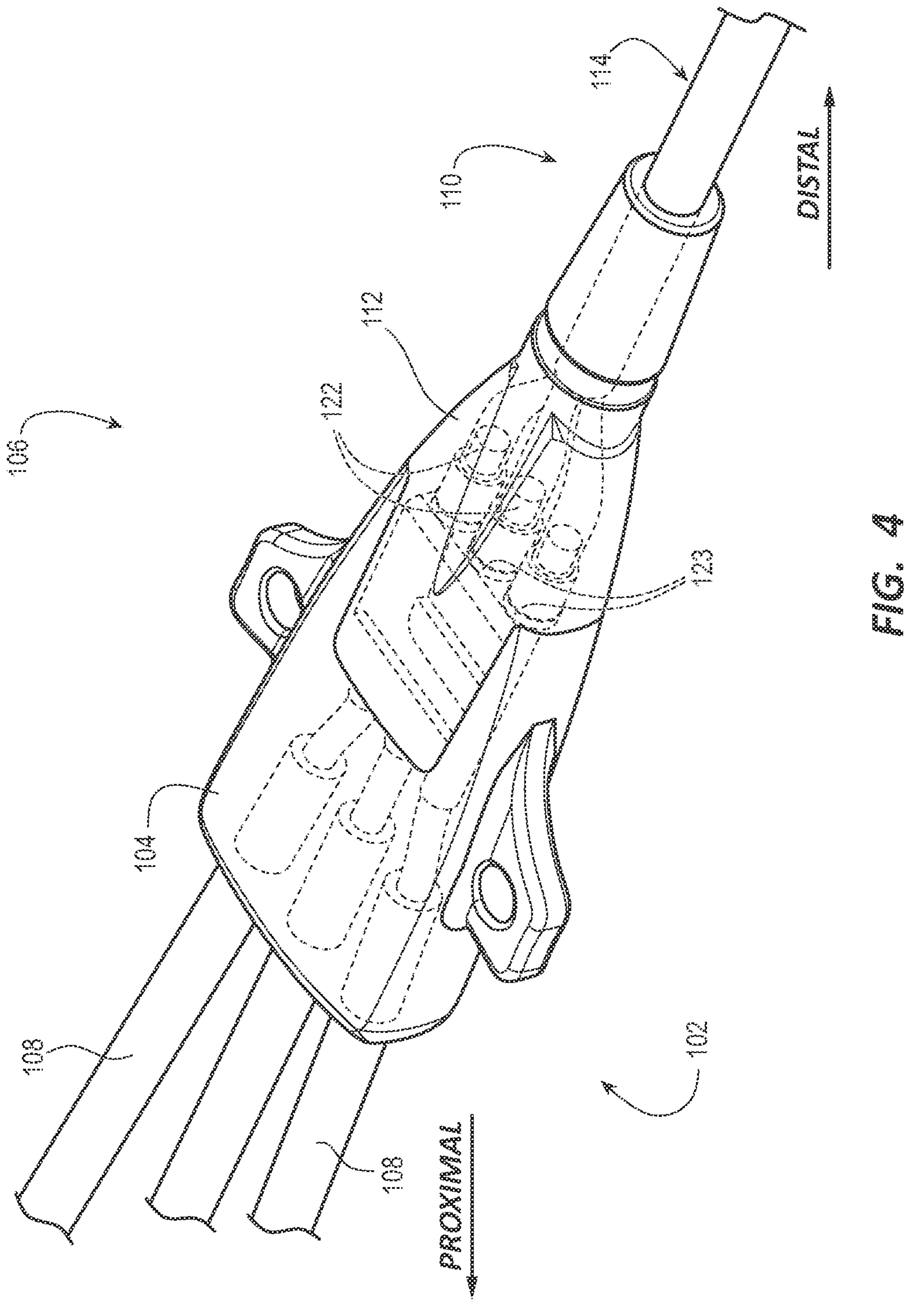
FIG. 4 illustrates the proximal catheter-hub piece and the distal catheter-hub piece in the connected state in accordance with some embodiments.

FIGS. 3 and 4 illustrate the proximal catheter-hub piece 104 and the distal catheter-hub piece 112 of the two-piece catheter hub 106 in the unconnected state and the connected state of the two-piece catheter 100 in accordance with some embodiments.

The proximal catheter-hub piece 104 of the two-piece catheter hub 106 includes one or more rigid tubes 116 (e.g., metal tubes) respectively disposed in one or more proximal catheter-hub lumens 118, thereby effectively extending the one-or-more proximal catheter-hub lumens 118 in connectors. The proximal catheter-hub piece 104 can be molded over the one-or-more rigid tubes 116 during manufacturing such that the one-or-more rigid tubes 116 extend from a distal end of the proximal catheter-hub piece 104. Alternatively, the one-or-more rigid tubes 116 are inserted into the one-or-more proximal catheter-hub lumens 118 during manufacturing such that the one-or-more rigid tubes 116 extend from the distal end of the proximal catheter-hub piece 104.

The distal catheter-hub piece 112 of the two-piece catheter hub 106 includes one or more distal catheter-hub lumens 120 including one or more mechanical gaskets 122 respectively disposed therein. The one-or-more mechanical gaskets 122 are configured to sit between abluminal surfaces of the one-or-more rigid tubes 116 and luminal surfaces of the one-or-more distal catheter-hub lumens 120 in the connected state of the two-piece catheter 100. The one-or-more mechanical gaskets 122 include, but are not limited to, 'O'-rings or cylinders. The one-or-more mechanical gaskets 122 can be formed of a compressible polymeric material such as a silicone. Use of a compressible polymeric material such as silicone is advantageous in that axial compression of the one-or-more mechanical gaskets 122 by compression annuli 123 when inserting the one-or-more rigid tubes 116 into the one-or-more distal catheter-hub lumens 120 forces the one-or-more mechanical gaskets 122 to radially expand in the limited space between the abluminal surfaces of the one-or-more rigid tubes 116 and the luminal surfaces of the one-or-more distal catheter-hub lumens 120, thereby creating one-or-more fluid-tight luminal seals between the proximal catheter-hub piece 104 and the distal catheter-hub piece 112 of the two-piece catheter hub 106 and respectively continuing the one-or-more proximal catheter-hub lumens 118 into the one-or-more distal catheter-hub lumens 120.

In an alternative to the foregoing, the distal catheter-hub piece 112 can instead include the one-or-more rigid tubes 116 respectively disposed in the one-or-more distal catheter-hub lumens 120. Likewise, the proximal catheter-hub piece 104 can instead include the one-or-more mechanical gaskets 122 respectively disposed in the one-or-more proximal catheter-hub lumens 118. It should be understood the foregoing description for the one-or-more rigid tubes 116, the one-or-more mechanical gaskets 122, and the like for the illustrated embodiments of the proximal catheter-hub piece 104 and the distal catheter-hub piece 112 apply to the one-or-more rigid tubes 116 when part of the distal catheter-hub piece 112, the one-or-more mechanical gaskets 122 when part of the proximal catheter-hub piece 104, and the like.

Continuing with the illustrated embodiments of the proximal catheter-hub piece 104 and the distal catheter-hub piece 112, the proximal catheter-hub piece 104 and the distal catheter-hub piece 112 include complementary connectors of a connection system configured to securely and, in some embodiments, irreversibly connect the proximal catheter-hub piece 104 and the distal catheter-hub piece 112 in the connected state of the two-piece catheter 100. "Irreversibly" connecting the proximal catheter-hub piece 104 and the distal catheter-hub piece 112 in this context should be understood to mean the proximal catheter-hub piece 104 and the distal catheter-hub piece 112 cannot be disconnected without tools or damage to the proximal catheter-hub piece 104 or the distal catheter-hub piece 112.

As to the connection system, the distal catheter-hub piece 112 can include an integral clip molded together with the distal catheter-hub piece 112 itself, the integral clip having tabbed arms 124 proximally extending from the distal catheter-hub piece 112. The proximal catheter-hub piece 104 can include complementary receivers such as surface recesses 126 configured to seat both the tabbed arms 124 and tabs 128 of the tabbed arms 124 therein in the connected state of the two-piece catheter 100. As best shown in FIG. 3, the tabbed arms 124 can extend from major sides of the distal catheter-hub piece 112 and the surface recesses 126 can be in major surfaces of the proximal catheter-hub piece 104. However, the tabbed arms 124 can alternatively extend from minor sides of the distal catheter-hub piece 112 and the surface recesses 126 can be in minor surfaces of the proximal catheter-hub piece 104. Due to greater design space across a width of the two-piece catheter hub 106, the complementary receivers can instead be longitudinal cavities inboard of the minor surfaces of the proximal catheter-hub piece 104 into which the tabbed arms 124 extending from the minor sides of the distal catheter-hub piece 112 are configured to insert, which is similar to that of common plastic buckles on backpacks and the like.

Figure 5:
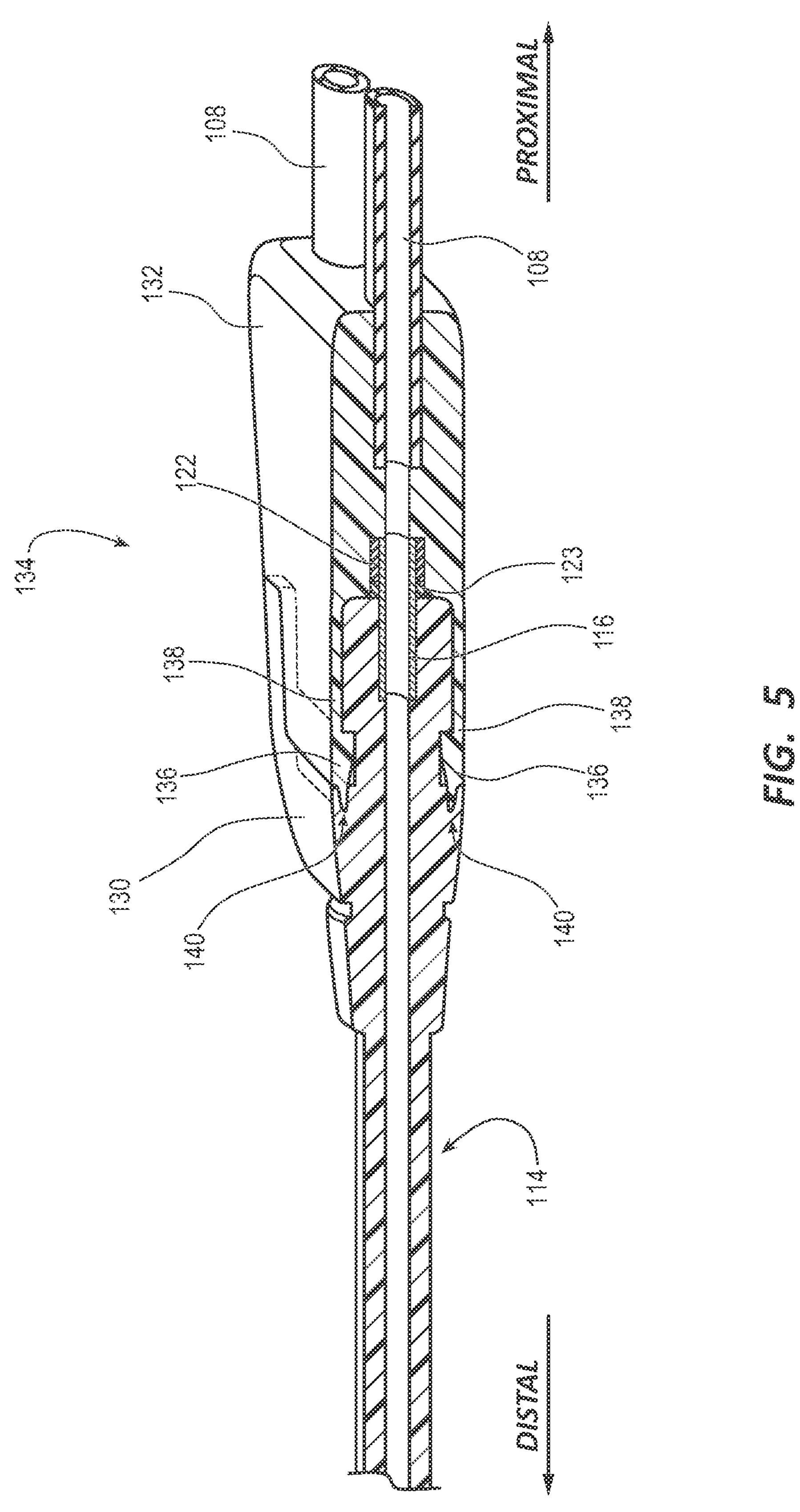
FIG. 5 illustrates another proximal catheter-hub piece and another distal catheter-hub piece of another two-piece catheter hub in the connected state in accordance with some embodiments.

FIG. 5 illustrates another proximal catheter-hub piece 130 and another distal catheter-hub piece 132 of another two-piece catheter hub 134 in the connected state of the two-piece catheter 100 in accordance with some embodiments.

As to irreversibly connecting the proximal catheter-hub piece 104 and the distal catheter-hub piece 112, the connection system can include additional features between the proximal catheter-hub piece 104 and the distal catheter-hub piece 112 configured for irreversibly connecting the proximal catheter-hub piece 104 and the distal catheter-hub piece 112. For example, the tabbed arms 124 of the distal catheter-hub piece 112 can include chamfered tips 136 like the tabbed arms 138 of the distal catheter-hub piece 132. The proximal catheter-hub piece 104 can include complementary receivers such as surface-undercut grooves 140 like those of the proximal catheter-hub piece 130, which are configured to seat therein the chamfered tips 136 of the tabbed arms 138 in the connected state of the two-piece catheter 100. When the chamfered tips 136 of the tabbed arms 138 are seated in the surface-undercut grooves 140, the tabbed arms 138 of the distal catheter-hub piece 132 cannot be readily lifted out of the complementary receivers of the proximal catheter-hub piece 130 without tools or damage to the proximal catheter-hub piece 130 or the distal catheter-hub piece 132, thereby irreversibly connecting the proximal catheter-hub piece 130 and the distal catheter-hub piece 132 in the connected state of the two-piece catheter 100.

In an alternative to the foregoing, the proximal catheter-hub piece 104 can instead include the integral clip having the tabbed arms 124 and, optionally, the chamfered tips 136 of the tabbed arms 138. Indeed, provided the one-or-more rigid tubes 116 are also disposed in the one-or-more proximal catheter-hub lumens 118 of the proximal catheter-hub piece 104, the integral clip effectively protects the one-or-more rigid tubes 116 from inadvertent damage. Likewise, the distal catheter-hub piece 112 can instead include the complementary receivers including the surface recesses 126 configured to seat the tabbed arms 124 and, optionally, the surface-undercut grooves 140 configured to seat the chamfered tips 136 of the tabbed arms 138. It should be understood the foregoing description for the tabbed arms 124 or 138, the complementary receivers, and the like for the illustrated embodiments of the proximal catheter-hub piece 104 and the distal catheter-hub piece 112 apply to the tabbed arms 124 or 138 when part of the proximal catheter-hub piece 104, the complementary receivers when part of the distal catheter-hub piece 112, and the like.

Figure 6:
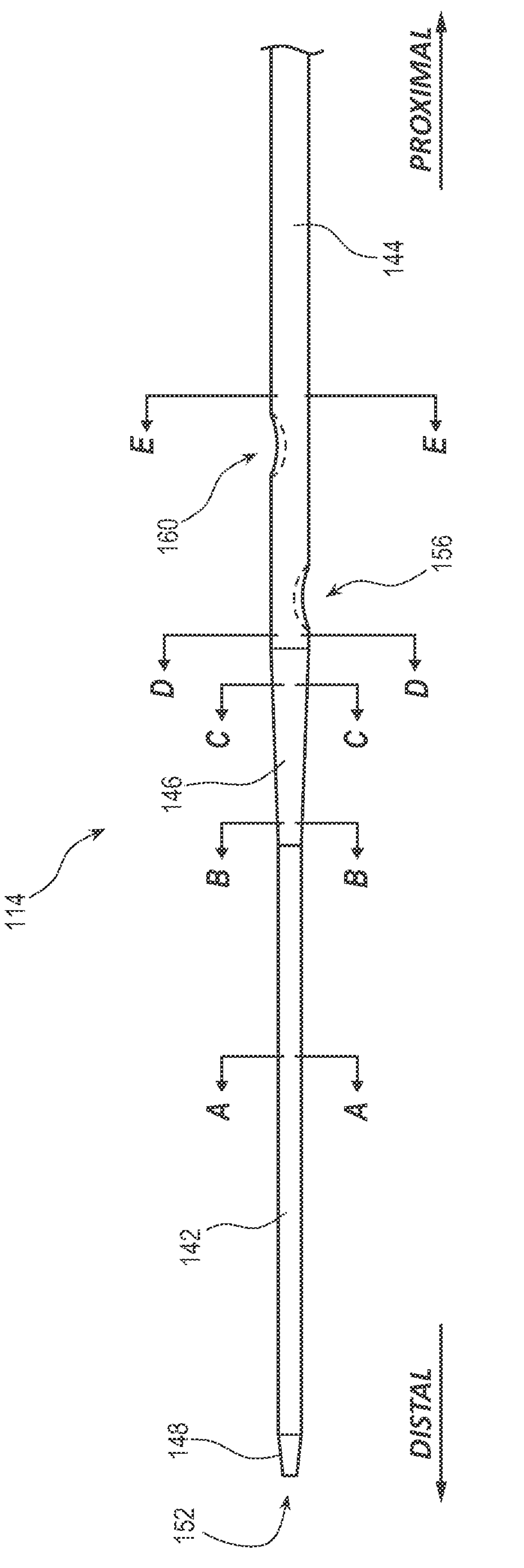
FIG. 6 illustrates a distal-end portion of a catheter tube of the two-piece catheter of FIGS. 1 and 2 in accordance with some embodiments.

FIG. 6 illustrates a distal-end portion of the catheter tube 114 of the two-piece catheter 100 in accordance with some embodiments. FIGS. 7-10 illustrate various transverse cross sections of the catheter tube 114 in accordance with some embodiments.

The catheter tube 114 is coupled to the distal catheter-hub piece 112 by a proximal-end portion of the catheter tube 114. As such, the one-or-more distal catheter-hub lumens 120 respectively continue as one or more catheter-hub lumens.

The catheter tube 114 can include a hard portion and a soft portion, wherein "hard" and "soft" are used in a relative sense in that the hard portion of the catheter tube 114 is harder than the soft portion of the catheter tube 114. For example, when the catheter tube 114 is part of a two-piece RICC, the catheter tube 114 includes the foregoing hard and soft portions; otherwise, the catheter tube 114 can be relatively soft with a compliance sufficient to advance the catheter tube 114 over a maneuver guidewire through a vasculature of a patient to a target location (e.g., the superior vena cava ["SVC"]).

The hard portion of the catheter tube 114 includes a first section 142 in a distal-end portion of the catheter tube 114, whereas the soft portion of the catheter tube 114 includes a second section 144 extending from the proximal-end portion of the catheter tube 114 to the distal-end portion thereof but proximal of the first section 142. Notwithstanding a tapered junction 146 of the catheter tube 114 including a proximal-end portion of the hard portion of the catheter tube 114 disposed therein, the soft portion of the catheter tube 114 is generally considered to include the junction 146 in view of its construction. Together, the foregoing arrangement of the first section 142 of the catheter tube 114, the second section 144 of the catheter tube 114, and the junction 146 possess both a column strength sufficient to prevent buckling of the catheter tube 114 when inserted into an insertion site established by a percutaneous puncture and a compliance sufficient to advance the catheter tube 114 through a vasculature of a patient to a target location (e.g., the SVC).

The first section 142 of the catheter tube 114 is in the distal-end portion of the catheter tube 114. The first section 142 includes a distal tip 148 having a relatively short taper configured to continue from a beveled tip of an introducer needle to an outer diameter of a remainder of the first section 142 when the introducer needle is disposed in the catheter tube 114 of the distal catheter piece 110. The short taper of the distal tip 148 is configured for immediate dilation of tissue about a percutaneous puncture established with the introducer needle up to the outer diameter of the remainder of the first section 142 of the catheter tube 114. The first section 142 also includes a proximal-end portion disposed in the receptacle of the junction 146 and fixedly coupled (e.g., solvent bonded, adhered, welded, etc.) thereto.

The first section 142 of the catheter tube 114 is formed of a first polymeric material having a first durometer. The first polymeric material can be polytetrafluoroethylene, polypropylene, or polyurethane, but the first polymeric material is not limited to the foregoing polymers. Polyurethane is advantageous in that the first section 142 of the catheter tube 114 can be relatively rigid at room-temperature but become more flexible in vivo at body temperature, which reduces irritation to vessel walls and phlebitis.

The second section 144 of the catheter tube 114 extends from the proximal-end portion of the catheter tube 114 to the distal-end portion thereof but proximal of the first section 142 of the catheter tube 114. The second section 144 includes a distal end coupled to the junction 146 and the proximal-end portion disposed in the distal catheter-hub piece 112 and fixedly coupled (e.g., solvent bonded, welded, adhered, etc.) thereto.

The second section 144 of the catheter tube 114 is formed of a second polymeric material having a second durometer less than the first durometer. The second polymeric material can be polyvinyl chloride, polyethylene, polyurethane, or silicone, but the second polymeric material is not limited to the foregoing polymers. In addition to that set forth above for polyurethane in the first section 142 of the catheter tube 114, polyurethane is advantageous in that it can be less thrombogenic than some other polymers.

The junction 146 of the catheter tube 114 couples the first and second sections 142 and 144 of the catheter tube 114 together. The junction 146 includes a receptacle in a distal-end portion including the proximal-end portion of the first section 142 of the catheter tube 114 disposed therein and fixedly coupled (e.g., solvent bonded, welded, adhered, etc.) thereto. The junction 146 also includes a flat-faced proximal end fixedly coupled (e.g., solvent bonded, welded, adhered, etc.) to a flat-faced distal end of the second section 144 of the catheter tube 114, which, as coupled, effectively terminates lumens of the second section 144 of the catheter tube 114 other than that corresponding to the primary lumen 150 of the two-piece catheter 100 from passing through the junction 146. The junction 146 also includes a taper over its length from a distal end to the proximal end configured for immediate dilation of tissue about the percutaneous puncture up to an outer diameter of the second section 144 of the catheter tube 114. An abluminal surface of the junction 146 smoothly transitions from an abluminal surface of the proximal-end portion of the first section 142 without an edge that catches on skin when inserted into an insertion site of a patient. In addition to the edge being minimal to negligible, the edge can include solvent-interdiffused polymeric material of the first polymeric material and the polymeric material of the junction 146, which smoothens the transition from the first section 142 of the catheter tube 114 to the junction 146.

The junction 146 of the catheter tube 114 is formed of the second polymeric material or a third polymeric material having a third durometer closer to the second durometer than the first durometer. Again, the second polymeric material can be polyvinyl chloride, polyethylene, polyurethane, or silicone, but the second polymeric material is not limited to the foregoing polymers.

Again, the first section 142 of the catheter tube 114 is formed of a first polymeric material having a first durometer, the second section 144 of the catheter tube 114 is formed of a second polymeric material having a second durometer less than the first durometer, and the junction 146 of the catheter tube 114 is formed of the second polymeric material or a third polymeric material having a third durometer closer to the second durometer than the first durometer. Being that each durometer of the second durometer and the third durometer is less than the first durometer, the soft portion of the catheter tube 114 including the second portion of the catheter tube 114 and the junction 146 is softer than the hard portion of the catheter tube 114 including the first portion of the catheter tube 114. In other words, the first durometer is greater than each durometer of the second durometer and the third durometer. Being that the first durometer is greater than each durometer of the second durometer and the third durometer, the hard portion of the catheter tube 114 including the first portion of the catheter tube 114 is harder than the soft portion of the catheter tube 114 including the second portion of the catheter tube 114 and the junction 146.

It should be understood the first durometer of the first polymeric material, the second durometer of the second polymeric material, and the third durometer of the third polymeric material can be on different scales (e.g., Type A or Type D), so the second durometer or the third durometer might not be numerically less than the first durometer. In other words, the first durometer material might not be numerically greater than the second durometer or the third durometer in view of the different scales. That said, the hardness of the second or third polymeric material can still be less than the hardness of the first polymeric material or the hardness of the first polymeric material can still be greater than the hardness of the second or third polymeric material because the different scales—each of which ranges from 0 to 100—are designed for characterizing different materials in groups of the materials having a like hardness.

Notwithstanding the foregoing, the first section 142 of the catheter tube 114, the second section 144 of the catheter tube 114, and the junction 146 can be formed of a same polymeric material or different polymeric materials having substantially equal durometers provided the column strength of the catheter tube 114 is sufficient to prevent buckling of the catheter tube 114 when inserted into an insertion site established by a percutaneous puncture and the compliance of the catheter tube 114 is sufficient to advance the catheter tube 114 through a vasculature of a patient to a target location.

Each extension leg of the one-or-more extension legs 108 is coupled to the proximal catheter-hub piece 104 by a distal-end portion of the extension leg. As such, the one-or-more proximal catheter-hub lumens 118 respectively continue as one or more extension-leg lumens.

Each extension leg of the one-or-more extension legs 108 typically includes a Luer connector coupled to the extension leg, through which Luer connector the extension leg and the extension-leg lumen thereof can be connected to another medical device.

Whether the two-piece catheter 100 is monoluminal with one lumen or multiluminal with a set of multiple lumens, the two-piece catheter 100 includes at least a primary lumen 150 (e.g., a distal lumen) in the connected state of the two-piece catheter 100, in which connected state the one-or-more catheter-tube lumens in the distal catheter piece 110 are respectively fluidly connected to the on-or-more extension leg lumens in the proximal catheter piece 102 across the two-piece catheter hub 106. The primary lumen 150 typically extends from a proximal end of the two-piece catheter 100 to a distal end of the two-piece catheter 100 such as from an opening of a corresponding Luer connector to a primary-lumen aperture 152 (e.g., a distal-lumen aperture) in a distal end of the two-piece catheter 100. When the two-piece catheter 100 has two or more lumens, the two-piece catheter 100 further includes at least a secondary lumen 154 (e.g., a medial lumen). The secondary lumen 154 typically extends from the proximal end of the two-piece catheter 100 to a distal-end portion of the two-piece catheter 100 such as from an opening of a corresponding Luer connector to a secondary-lumen aperture 156 (e.g., a medial-lumen aperture) in the distal-end portion of the catheter tube 114 proximal of the primary-lumen aperture 152. When the two-piece catheter 100 has three or more lumens, the two-piece catheter 100 further includes at least a tertiary lumen 158 (e.g., a proximal aperture). The tertiary lumen 158 typically extends from the proximal end of the two-piece catheter 100 to the distal-end portion of the two-piece catheter 100 such as from an opening of a corresponding Luer connector to a tertiary-lumen aperture 160 (e.g., a proximal-lumen aperture) in the distal-end portion of the catheter tube 114 proximal of the secondary-lumen aperture 156. Notwithstanding the foregoing, each lumen of the secondary lumen 154 and the tertiary lumen 158 can distally extend slightly farther than the secondary-lumen aperture 156 and the tertiary-lumen aperture 160, respectively, in view of different manufacturing methods. As set forth above, however, the flat-faced proximal end of the junction 146 is fixedly coupled (e.g., solvent bonded, welded, adhered, etc.) to the flat-faced distal end of the second section 144 of the catheter tube 114, which, as coupled, effectively terminates lumens such as the secondary and tertiary lumens 154 and 158 from passing through the junction 146.

A set forth above, it could be difficult to timely discern whether blood flashback has occurred and access to a blood-vessel lumen established during any given RICC introduction with a 30-40 cm introducer needle. As such, two-piece catheters configured as RICCs such those provided herein advantageously allow clinicians to use shorter, less cumbersome introducer needles with the distal catheter piece 110, which, in turn, also allows the clinicians to quickly discern whether blood flashback has occurred and access to a blood-vessel lumen established during any given RICC introduction.

Notably, the existing catheters set forth above (see Background) are inserted using the Seldinger technique. Such catheters do not benefit in the same way as the RICCs provided herein when the existing catheters are two-piece catheters. Indeed, increasing the number of catheter pieces in the existing catheters is disadvantageous in that one of the reasons the RICCs are currently being developed is to decrease the overall number of components and steps used in the Seldinger technique for the existing catheters.

Methods

Methods of the two-piece catheter 100 include a method of using the two-piece catheter 100. Such a method includes a catheter-obtaining step, a needle tract-establishing step, a needle-withdrawing step, and a catheter hub-clipping step.

The catheter-obtaining step includes obtaining the two-piece catheter 100 including the distal catheter piece 110 and the proximal catheter piece 102. As set forth above, the distal catheter piece 110 includes the catheter tube 114 coupled to the distal catheter-hub piece 112 by the proximal-end portion of the catheter tube 114.

The needle tract-establishing step includes establishing a needle tract from an area of skin to a blood-vessel lumen of a patient with an introducer needle disposed in an introducing lumen of the distal catheter piece 110. The introducing lumen is a combination of a distal catheter-hub lumen and a catheter-tube lumen making up a portion of the primary lumen 150 of the two-piece catheter 100—particularly in the unconnected state of the two-piece catheter 100. In the needle tract-establishing step, the introducer needle is disposed in the distal catheter piece 110 such that a needle tip of the introducer needle extends out of an introducing-lumen aperture (e.g., the primary-lumen aperture 152) of the introducing lumen.

The needle-withdrawing step includes withdrawing the introducer needle from the introducing lumen.

The catheter hub-clipping step includes clipping together the distal catheter-hub piece 112 and the proximal catheter-hub piece 104. If the integral clip is part of the distal catheter-hub piece 112 as shown in FIGS. 1 and 3, the catheter hub-clipping step includes clipping the integral clip of the distal catheter-hub piece 112 onto the proximal catheter-hub piece 104, in which the tabs 128 of the tabbed arms 124 of the integral clip seat in the surface recesses 126 in the major or minor surfaces of the proximal catheter-hub piece 104. If, however, the integral clip is part of the proximal catheter-hub piece 104, the catheter hub-clipping step includes clipping the integral clip of the proximal catheter-hub piece 104 onto the distal catheter-hub piece 112, in which the tabs 128 of the tabbed arms 124 of the integral clip seat in the surface recesses 126 in the major or minor surfaces of the distal catheter-hub piece 112. Regardless, upon clipping together the distal catheter-hub piece 112 and the proximal catheter-hub piece 104, the one-or-more catheter-tube lumens of the catheter tube 114 respectively fluidly connect to the one-or-more extension-leg lumens of the one-or-more extension legs 108 coupled to the proximal catheter-hub piece 104 of the proximal catheter piece 102.

The method can further include an access guidewire-advancing step, a first catheter-advancing step, and an access guidewire-withdrawing step. The access guidewire-advancing step includes advancing an access guidewire disposed in a needle lumen of the introducer needle into the blood-vessel lumen beyond the needle tip. The first catheter-advancing step includes initially advancing the two-piece catheter 100 into the blood-vessel lumen over the access guidewire. If the two-piece catheter 100 is a RICC, the first catheter-advancing step includes advancing a distal-end portion of the first section 142 of the catheter tube 114 into the blood-vessel lumen over the introducer needle using the access guidewire as a guide. The access guidewire-withdrawing step includes withdrawing the access guidewire together with the introducer needle when withdrawing the introducer needle from the introducing lumen.

The method can further include a maneuver guidewire-advancing step, a second catheter-advancing step, and a maneuver guidewire-withdrawing step. The maneuver guidewire-advancing step includes advancing a maneuver guidewire into the blood-vessel lumen and to a target location by way of the primary lumen 150 of the two-piece catheter 100. Again, the primary lumen 150 is established by clipping together the distal catheter-hub piece 112 and the proximal catheter-hub piece 104. The second catheter-advancing step includes advancing the two-piece catheter 100 farther into the blood-vessel lumen over the maneuver guidewire. If the two-piece catheter 100 is a RICC, the second catheter-advancing step includes advancing a remainder of the distal-end portion of the first section 142 of the catheter tube 114 into the blood-vessel lumen up to a proximal-end portion of the second section 144 of the catheter tube 114 using the maneuver guidewire as a guide. Advancing the catheter in accordance with the second catheter-advancing step is stopped when the distal end of the two-piece catheter 100 arrives at the target location. The maneuver guidewire-withdrawing step includes withdrawing the maneuver guidewire and leaving the two-piece catheter 100 in place in the patient.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A two-piece catheter, comprising:

a proximal catheter piece including:

a proximal catheter-hub piece of a two-piece catheter hub; and one or more extension legs respectively including one or more extension-leg lumens, each extension leg of the one or more extension legs coupled to the proximal catheter-hub piece by a distal-end portion of each extension leg; and a distal catheter piece including:

a distal catheter-hub piece of the two-piece catheter hub;

a catheter tube including one or more catheter-tube lumens, the catheter tube coupled to the distal catheter-hub piece by a proximal-end portion of the catheter tube, wherein a first catheter-hub piece of the proximal catheter-hub piece or the distal catheter-hub piece includes one or more rigid tubes respectively disposed in one or more catheter-hub lumens thereof, wherein a second catheter-hub piece of the proximal catheter-hub piece or the distal catheter-hub piece includes one or more gaskets respectively disposed in the one or more catheter-hub lumens thereof configured to sit between one or more rigid tubes and the one or more catheter-hub lumens, and wherein the two-piece catheter has a connected state in which the proximal catheter-hub piece is connected to the distal catheter-hub piece such that the one or more catheter-tube lumens are respectively fluidly connected to the one or more extension-leg lumens across the two-piece catheter hub by one or more fluid-tight luminal seals due to compression of the one or more gaskets in the one or more catheter-hub lumens of the first catheter-hub piece of the proximal catheter-hub piece or the distal catheter-hub piece by compression annuli of the second catheter-hub piece of the proximal catheter-hub piece or the distal catheter-hub piece.

2. The two-piece catheter of claim 1, wherein the proximal catheter-hub piece includes the one or more rigid tubes respectively disposed in one or more proximal catheter-hub lumens, the one or more rigid tubes and the compression annuli extending from a distal end of the proximal catheter-hub piece.

3. The two-piece catheter of claim 2, wherein the distal catheter-hub piece includes the one or more gaskets respectively disposed in one or more distal catheter-hub lumens, the one or more gaskets axially compressed in the one or more distal catheter-hub lumens by the compression annuli and radially compressed between the one or more rigid tubes and the one or more distal catheter-hub lumens, respectively, in the connected state of the two-piece catheter hub.

4. The two-piece catheter of claim 1, wherein the distal catheter-hub piece includes the one or more rigid tubes respectively disposed in one or more distal catheter-hub lumens, the one or more rigid tubes and the compression annuli extending from a proximal end of the distal catheter-hub piece.

5. The two-piece catheter of claim 4, wherein the proximal catheter-hub piece includes the one or more gaskets respectively disposed in one or more proximal catheter-hub lumens, the one or more gaskets axially compressed in the one or more distal catheter-hub lumens by the compression annuli and radially compressed between the one or more rigid tubes and the one or more proximal catheter-hub lumens, respectively, in the connected state of the two-piece catheter hub.

6. The two-piece catheter of claim 1, wherein the distal catheter-hub piece includes an integral clip having tabbed arms proximally extending from the distal catheter-hub piece and the proximal catheter-hub piece includes surface recesses configured to seat tabs of the tabbed arms therein in the connected state of the two-piece catheter hub.

7. The two-piece catheter of claim 6, wherein the proximal catheter-hub piece includes surface-undercut grooves configured to seat tips of the tabbed arms therein in the connected state of the two-piece catheter hub.

8. The two-piece catheter of claim 6, wherein the tabbed arms extend from major sides of the distal catheter-hub piece and the surface recesses are in major surfaces of the proximal catheter-hub piece.

9. The two-piece catheter of claim 6, wherein the tabbed arms extend from minor sides of the distal catheter-hub piece and the surface recesses are in minor surfaces of the proximal catheter-hub piece.

10. The two-piece catheter of claim 1, wherein the proximal catheter-hub piece includes an integral clip having tabbed arms distally extending from the proximal catheter-hub piece and the distal catheter-hub piece includes surface recesses configured to seat tabs of the tabbed arms therein in the connected state of the two-piece catheter hub.

11. The two-piece catheter of claim 10, wherein the distal catheter-hub piece includes surface-undercut grooves configured to seat tips of the tabbed arms therein in the connected state of the two-piece catheter hub.

12. The two-piece catheter of claim 10, wherein the tabbed arms extend from major sides of the proximal catheter-hub piece and the surface recesses are in major surfaces of the distal catheter-hub piece.

13. The two-piece catheter of claim 10, wherein the tabbed arms extend from minor sides of the proximal catheter-hub piece and the surface recesses are in minor surfaces of the distal catheter-hub piece.

14. The two-piece catheter of claim 1, wherein the two-piece catheter includes a set of three lumens in the connected state of the two-piece catheter, the set of three lumens including a primary lumen, a secondary lumen, and a tertiary lumen.

15. The two-piece catheter of claim 14, wherein the primary lumen has a primary-lumen aperture in a distal end of the two-piece catheter, the secondary lumen has a secondary-lumen aperture in a side of the catheter tube proximal of the primary-lumen aperture, and the tertiary lumen has a tertiary-lumen aperture in the side of the catheter tube proximal of the secondary-lumen aperture.

16. A method of using a two-piece catheter, comprising:

obtaining the two-piece catheter including a distal catheter piece and a proximal catheter piece, the distal catheter piece including a catheter tube coupled to a distal catheter-hub piece of a two-piece catheter hub, and the proximal catheter piece including one or more extension legs coupled to a proximal catheter-hub piece of the two-piece catheter hub;

establishing a needle tract from an area of skin to a blood-vessel lumen of a patient with an introducer needle disposed in an introducing lumen of the distal catheter piece such that a needle tip of the introducer needle extends out of an introducing-lumen aperture of the introducing lumen;

withdrawing the introducer needle from the introducing lumen; and clipping together the distal catheter-hub piece and the proximal catheter-hub piece, a first catheter-hub piece of the distal catheter-hub piece or the proximal catheter-hub piece including one or more rigid tubes respectively disposed in one or more catheter-hub lumens thereof, and the second catheter-hub piece of the distal catheter-hub piece or the proximal catheter-hub piece including one or more gaskets respectively disposed in the one or more catheter-hub lumens thereof configured to sit between the one or more rigid tubes and the one or more catheter-hub lumens, thereby respectively connecting across the two-piece catheter hub one or more catheter-tube lumens of the catheter tube and one or more extension-leg lumens of the one or more extension legs with one or more fluid-tight luminal seals due to compression of the one or more gaskets in the one or more catheter-hub lumens of a first catheter-hub piece of the proximal catheter-hub piece or the distal catheter-hub piece by compression annuli of the second catheter-hub piece of the proximal catheter-hub piece or the distal catheter-hub piece.

17. The method of claim 16, wherein clipping together the distal catheter-hub piece and the proximal catheter-hub piece includes clipping an integral clip of the distal catheter-hub piece onto the proximal catheter-hub piece such that tabs of arms of the integral clip seat in surface recesses in major or minor surfaces of the proximal catheter-hub piece.

18. The method of claim 16, wherein clipping together the distal catheter-hub piece and the proximal catheter-hub piece includes clipping an integral clip of the proximal catheter-hub piece onto the distal catheter-hub piece such that tabs of arms of the integral clip seat in surface recesses in major or minor surfaces of the distal catheter-hub piece.

19. The method of claim 16, further comprising:

advancing an access guidewire disposed in a needle lumen of the introducer needle into the blood-vessel lumen beyond the needle tip;

advancing a distal-end portion of a first section of the catheter tube into the blood-vessel lumen over the introducer needle using the access guidewire as a guide; and withdrawing the access guidewire together with the introducer needle when withdrawing the introducer needle from the introducing lumen.

20. The method of claim 19, further comprising:

advancing a maneuver guidewire into the blood-vessel lumen and to a target location by way of a primary lumen of the two-piece catheter established by clipping together the distal catheter-hub piece and the proximal catheter-hub piece;

advancing a remainder of the distal-end portion of the first section of the catheter tube into the blood-vessel lumen up to a proximal-end portion of a second section of the catheter tube using the maneuver guidewire as a guide, stopping the advancing when a distal end of the catheter tube arrives at the target location; and withdrawing the maneuver guidewire and leaving the two-piece catheter in place in the patient.

* * * * *